United States Patent [19]

DeMeester et al.

[11] Patent Number: 4,686,692
[45] Date of Patent: Aug. 11, 1987

[54] COMPUTED TOMOGRAPHY PATIENT LOCALIZATION SCANNING

[75] Inventors: Gordon D. DeMeester, Wickliffe; Rodney A. Mattson, Mentor, both of Ohio

[73] Assignee: Picker International Inc., Highland Heights, Ohio

[21] Appl. No.: 722,672

[22] Filed: Apr. 12, 1985

[51] Int. Cl.$^4$ .................................. G01N 23/04
[52] U.S. Cl. ........................................ 378/4; 378/22; 378/901
[58] Field of Search .................. 378/4, 20, 901, 21–26; 358/111; 364/414

[56] References Cited

U.S. PATENT DOCUMENTS

| | | | |
|---|---|---|---|
| 3,745,245 | 7/1973 | Yunde et al. | 358/111 |
| 3,983,399 | 9/1976 | Cox, Jr. et al. | 378/4 |
| 4,048,505 | 9/1977 | Hounsfield | 378/19 |
| 4,123,657 | 10/1978 | Krippner et al. | 378/19 |
| 4,174,481 | 11/1979 | Liebetruth | |
| 4,295,195 | 10/1981 | Hounsfield | 378/19 |
| 4,504,858 | 3/1985 | Franke | 358/111 |
| 4,570,263 | 2/1986 | Liebetruth | 378/4 |
| 4,570,264 | 2/1986 | Liebetruth | 378/4 |

OTHER PUBLICATIONS

Imatron advertisement and manual p. 6–33, Imatron Inc., May 29, 1984 and Nov. 1985.
"Computerized Multiple X-rays Give a New View of the Body's Interior" by H. Zaklad, Electronics, vol. 49, No. 21, pp. 89–94, Oct. 14, 1976.

Primary Examiner—Craig E. Church
Assistant Examiner—John C. Freeman
Attorney, Agent, or Firm—Watts, Hoffmann, Fisher & Heinke Co.

[57] ABSTRACT

Method and apparatus for a computed tomography patient localization scan. A source of radiation that orbits a patient during a normal computed tomography scan is fixed relative an array of radiation detectors. The patient is then moved in a direction generally perpendicular to the plane of the radiating source and array to obtain a first shadowgraph data set. The source is orbited a small amount and the patient is again moved relative the source and detector array to obtain a second shadowgraph set of data. The two sets of data are then interleaved to obtain a shadowgraph image having higher resolution than either the first or second shadowgraph.

10 Claims, 8 Drawing Figures

COMPUTED TOMOGRAPHY PATIENT LOCALIZATION SCANNING

1. Technical Field

The present invention relates generally to a computed tomography scanner and more specifically to a new and improved scanning method and apparatus for locating a tomographic plane to be scanned.

2. Background Art

In computed tomography (CT), a subject is irradiated from a number of directions and the intensity of radiation passing through the subject is detected. This procedure provides information sufficient to generate a cross-sectional mapping of attenuation within the subject. The procedure for generating this mapping is known within the computed tomography art as filtered back projection. Various methods of reconstruction imaging have been developed as the computer tomography art has matured. In most all, if not all, commercial CT scanners presently known to applicants, x-ray attenuation data are lourier transformed, filtered, and then retransformed prior to back projection.

Computed tomography scanners have evolved in stages. An initial scanner used a single x-ray source and single detector which traversed back and forth in unison obtaining intensity information for use in the back projection process. Second and third generation scanners employed detector arrays rather than individual detectors. In second generation scanners these arrays traversed and orbited while in third generation they simply orbit with the x-ray source. A fourth generation scanner employs a circular array of detectors circumscribing a patient region of interest. The x-ray source orbits with respect to this circular detector array to irradiate' the subject from a plurality of positions.

One example of a fourth generation computed tomography scanner is marketed under the designation Synerview 1200 by Picker International, Inc. of Cleveland, OH. In this scanner, the detector array includes 1200 closely spaced detectors forming a circle whose diameter is greater than the diameter of the circular path followed by the x-ray tube as it orbits the patient. Stated another way, x-radiation from the tube travels a shorter distance between tube and patient than between the patient and detector array after traversing the patient.

One requirement of computed tomography scanners is a procedure for accurately positioning the patient prior to conducting a computed tomography scan. If the diagnosing physician is interested in viewing the internal structure of a particular organ, it is inefficient and undesirable to scan the entire body. Instead, only a region of interest including the organ or other body part of concern is scanned.

To accomplish this positioning the x-ray source can be locked in a stationary position relative to the detector array and the patient moved past the array as the source irradiates the patient. X-ray intensity data from a group of detectors is sensed sequentially at each of a series of data collection positions. At each data collection position a new row of intensity information is gathered. After the patient has moved past the detector array an image similar to a conventional digital x-ray shadowgraph image is created. Such an image does not represent a cross-sectional image but instead, depicts the transmissivity of the subject alone paths from the fixed x-ray source to individual elements of the detector array. While not providing the resolution and/or information of a computed tomography scan, such a patient localization scan can be used to locate structure within the subject in anticipation of positioning that subject for a complete CT scan.

DISCLOSURE OF INVENTION

The present invention relates to method and apparatus for increasing resolution in a patient localization scan. Shadowgraph resolution is increased so that the shadowgraph image more accurately depicts the internal structure of the patient.

A patient is moved longitudinally through a series of spaced data collection positions. Radiation is directed from a stationary radiation source through the patient to an array of radiation detectors. After attenuation by the subject, the radiation intensity is detected at each of the data collection positions to generate a first set of shadowgraph data. The radiation from the x-ray source is then directed along slightly different trajectories through the subject. The radiation intensities along these slightly different trajectories are detected as the patient is again moved relative the detector array and a second set of shadowgraph data generated. Finally, the two sets of data are interleaved to form a composite image having resolution greater than either individual set of data.

In a preferred embodiment of the invention, the second set of intensity readings are obtained by indexing or orbiting the x-ray source a small amount between successive data gathering scans. The x-radiation then is emitted from a second stationary source position and traverses the patient along different trajectories as the patient is moved relative the detector array as the second set of data is generated.

In one commercial computed tomography scanner the spacing between detectors within the detector array is approximately 0.6°. In a preferred interleaved patient localization scan, after the first set of shadowgraph data is obtained, the x-ray tube is indexed through an angular distance of 0.3° i.e. ½ of the angular spacing between detectors. with a description of a preferred embodiment of the invention, a second set of shadowgraph data can then be interleaved with the first to increase the resolution of the resulting shadowgraph image.

Sequentially positioning the x-ray tube in a series of positions which are fixed relative to a patient and performing multiple longitudinal scans can be used to create contrast images. A radiation contrast agent is injected into the patient after a first and before a second of two equally timed longitudinal scans. Digital subtraction angiography techniques are then utilized to image contrast agent flow within the patient. This contrast study approximates the image produced by a digital x-ray unit with perhaps less resolution. While continual use of a CT scanner for such digital subtraction or other digital studies would be inefficient, an occasional such use in a hospital with no digital x-ray unit available for such a study is contemplated.

Accordingly one object of the invention is to obtain enhanced resolution from patient localization scans conducted with a computed tomography scanner. This and other objects, advantages and features of the invention will become better understood when a detailed description of a preferred embodiment of the invention is described in conjunction with the accompanying drawings.

BEST MODE FOR CARRYING OUT THE INVENTION

Figure 1:
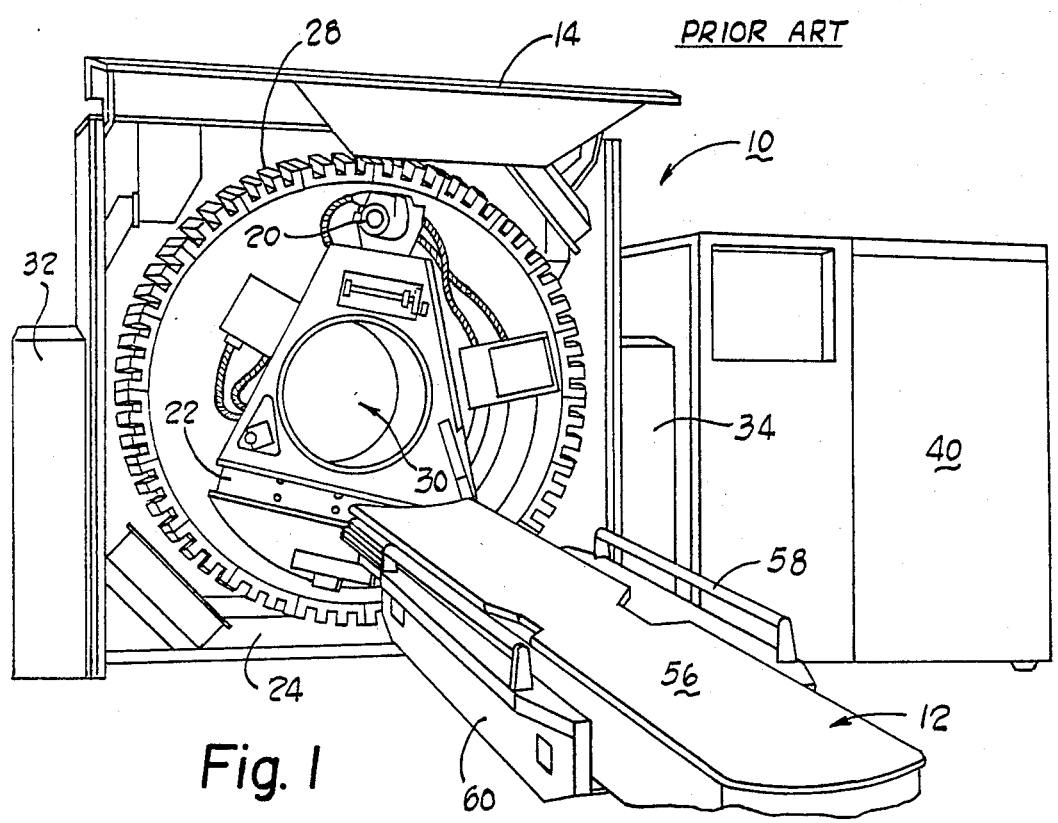
FIG. 1 is a perspective view of a computed tomography scanner having a motorized couch for moving the patient relative to a scanning x-ray tube and stationary detector array.

Turning now to the drawings, and in particular FIG. 1, a computed tomography scanner 10 and a patient couch 12 are illustrated. The scanner 10 is illustrated with a front panel 14 pivoted away from its in use position to show the internal components of the scanner 10. The scanner 10 includes a rotatable x-ray source 20 mounted on a rotatable frame 22. The frame 22 is journalled for rotation within a gantry 24. Coupled to and supported by the gantry 24 are a plurality of x-radiation detectors forming a detector array 28. During operation radiation from the source 20 passes across a patient aperture 30 in a plane 32 to the detector array 28.

During computed tomography scanning, the x-ray source 20 is rotated by a motor (not shown) in a circular orbit around a patient aperture 30. A generally planar and spread beam of x-radiation from the source 20 impinges upon a group of detectors forming a part of the detector array 28. As the source rotates, different detectors are irradiated and intensity information is obtained from these detectors. Output signals from the detector array 28 are processed by components that convert the radiation into visible light, to an analog electric signal, to a frequency, and then to digital attenuation values. A computer 40 stores this data derived from these values and uses it for reconstruction processing. As seen most clearly in FIGS. 2 and 3, the patient couch 12 includes a base 52 supporting a movable frame 54 which supports a top 56. The top 56 and frame 54 are bounded on either side by retractable handles 58 and an arm rest 60. To position a patient in a patient examination position in the patient aperture for computed tomography scanning, a frame lift motor (not shown) raises the frame 54, top 56 and handles 58 from the position shown in solid in FIG. 2 to the position shown in phantom. In this raised position, the patient can be moved into and out of the patient aperture 30.

Figure 5:
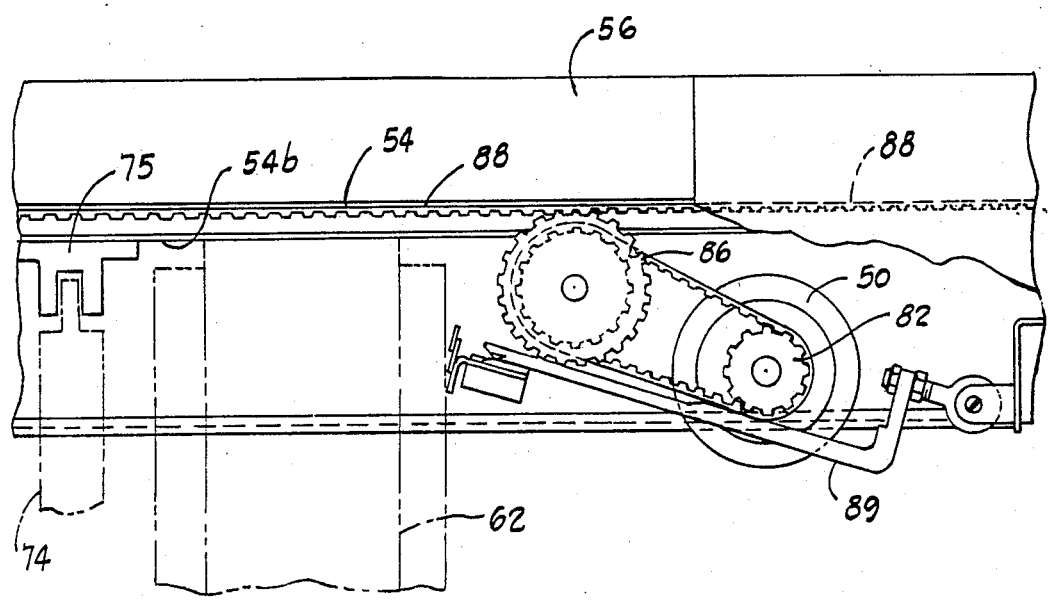
FIG. 5 is a side elevation view, partly in section, of the FIG. 4 drive.

A longitudinal drive mechanism for the couch frame 54 and top 56 is seen in FIG. 5. One of two pedestal supports 62, is shown supporting the frame 54. This support 62 is coupled to a second pedestal (not shown) by a shaft and rack and pinion drive so that the two pedestal supports move in unison as the frame is raised and lowered. A motor driven screw jack 74 is coupled to a mounting block 75 which engages a bottom surface 54b of the frame 54.

Figure 4:
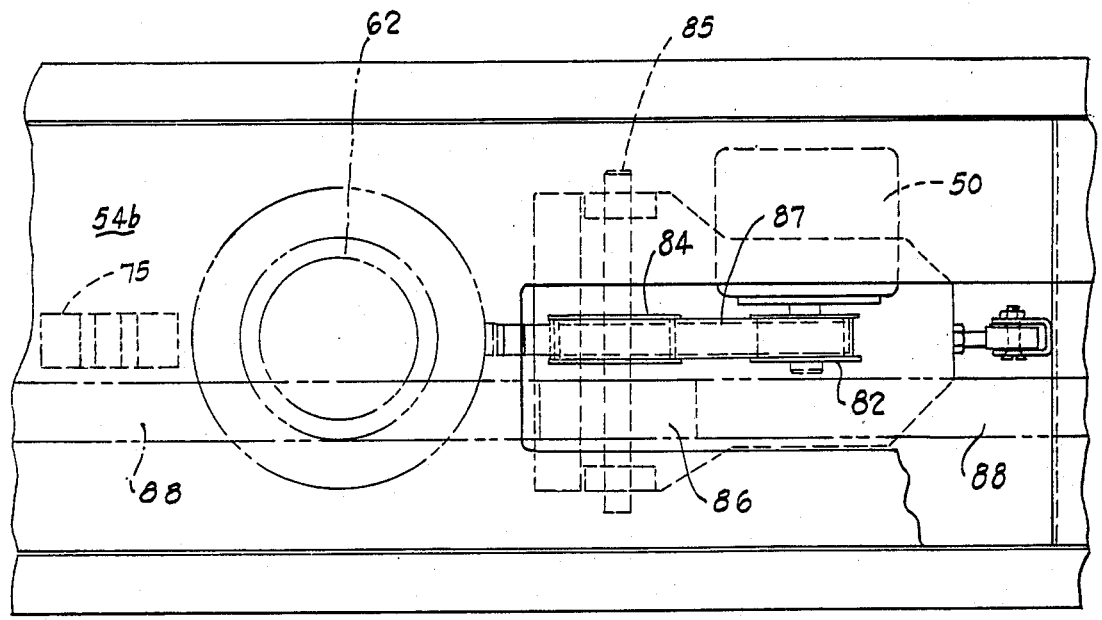
FIG. 4 is a top plan view of a couch frame showing a drive for moving a patient support into and out of a scanner aperture.

Longitudinal movement of the top 56 with respect to the couch frame 54 is provided by a D.C. motor 50 mounted within the frame 54. A drive pulley 82 mounted to a motor drive shaft is rotated in either of two directions. A pulley 84 (FIG. 4) mounted to a shaft 85 journaled in the frame 54 is connected to the drive pulley 82 by a belt 87 and rotates in response to energization of the motor 50. A gear 86 mounted on the shaft 85 engages an elongated gear belt 88 coupled to the movable top 56 so that rotation of the gear 86 exerts a force on the moveable top 56. Controlled energization of the motor 50 drives the gear belt and attached top 56 into and out of the aperture 30.

Figure 3:
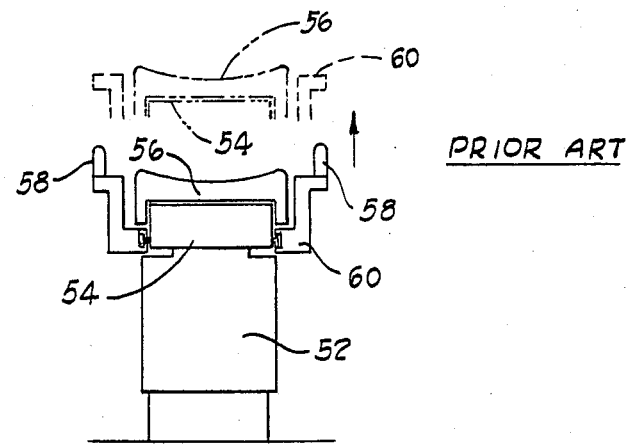
FIG. 3 is an end elevation view of the FIG. 2 couch.
Figure 3A:
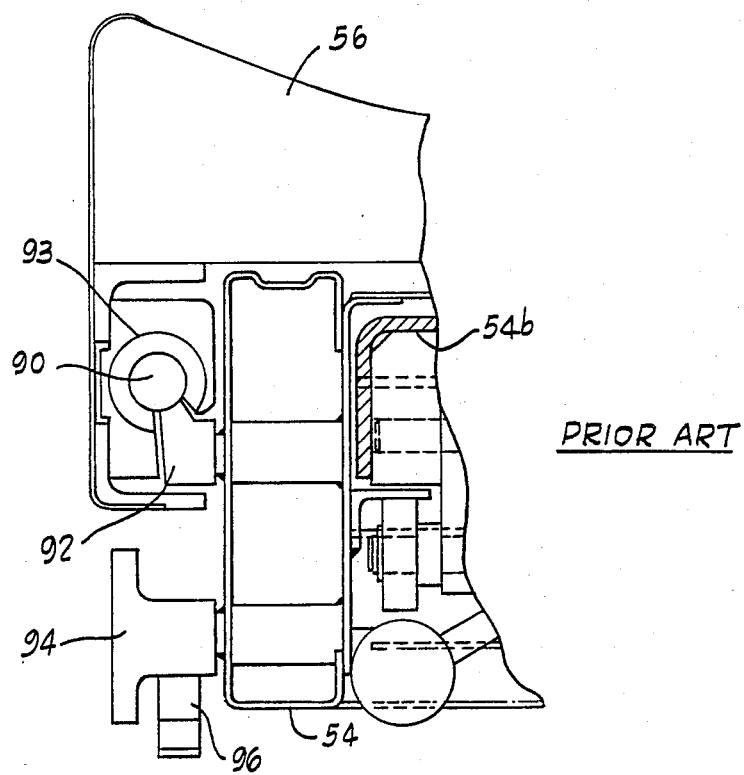
FIG. 3A is an enlarged partially sectioned, view of a couch top and its support.

The top 56 and frame 54 coact along two bearing rails 90 (only one of which is seen in FIG. 3A). Each rail is mounted on a shaft support block 92 (one of which is shown in FIG. 3A). The rails 90 each engage bearings 93 running the length of the moveable top 56. Directly beneath the rail 90 (FIG. 3A) are side rails 94 which support the arm rests 60 (FIG. 3).

Figure 2:
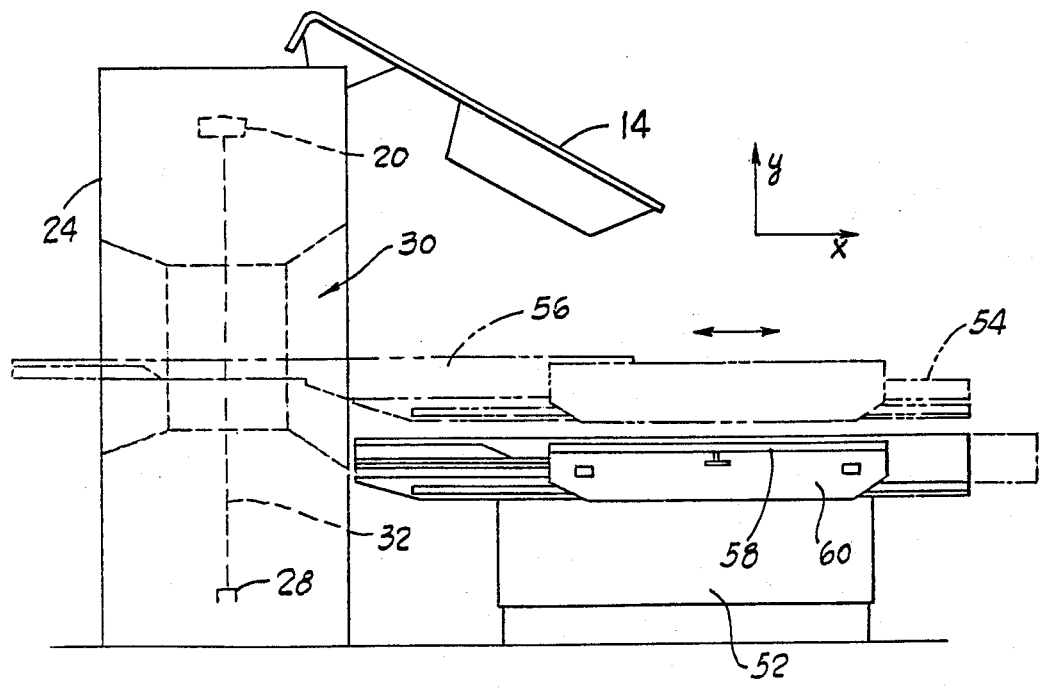
FIG. 2 is an side elevation view of a patient couch having a motor for moving the patient longitudinally into and out of a scanner patient aperture.

As has been indicated the patient couch 12 is motorized so that a patient placed on the couch can be moved into the scanner aperture 30. The patient is moved into the aperture 30 so that radiation from the tube 20 passes through the patient cross-section 32 (FIG. 2).

In preparation for cross-sectional scanning, a shadowgraph patient image is obtained. The x-ray tube 20 is fixed with respect to the gantry 24 and a beam of x-radiation is directed through the patient to a segment of adjacent detectors of the detector array 28. The x-ray tube 20 remains energized as the motor 50 continuously moves the patient axially of the aperture 30 and through the beam of radiation. X-radiation data from the energized x-ray detector segment is sensed and stored for the time period in which the patient is driven with respect to the scanner through a first longitudinal scan. During this first scan, movement of the top 56 is coordinated with radiation attenuation sensing so the data stored in the computer is organized in a rectangular array of pixels of attenuation data. In one embodiment of the invention for use with a 600 detector scanner, the radiation output from 128 adjacent detectors is sampled every millimeter at 128 different patient/scanner positions to obtain a 128 by 128 pixel shadowgraph data set.

After the first longitudinal scan is conducted, the source 20 is orbitally indexed a small amount to provide a second shadowgraph data set. In a 600 detector scanner, where the spacing between detectors is 0.6 degrees, the source is moved 0.3 degrees from its original position. The motor 50 is then energized to reverse the longitudinal scanning direction. The top 56 then moves in an opposite direction as a second set of shadowgraph data is obtained. The pixel data for each of the two shadowgraph images is then interleaved by the computer 40 to obtain a resultant shadowgraph of 256 by 128 pixels having twice the data set resolution of either individual longitudinal scan.

Figure 7:
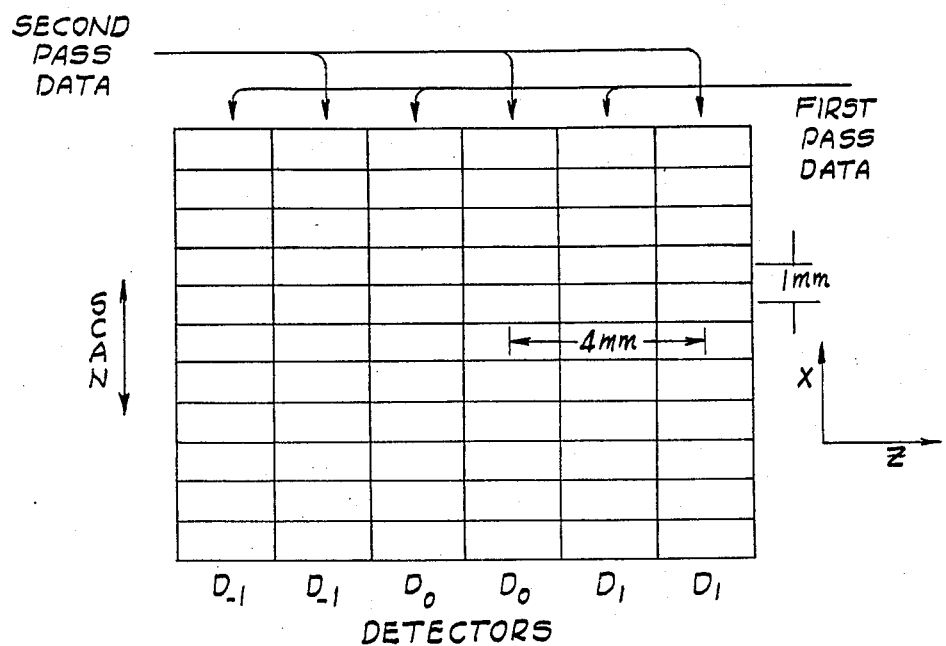
FIG. 7 is a mapping of interleaved intensity data showing increased image resolution through practice of the invention.

A grid like mapping (FIG. 7) of data from the 128 detectors is created. Along the longitudinal direction the center-to-center spacing between adjacent data regions is 1 mm. Without multiple scans the detector spacing is approximately 4 mm but with the interleaving of data from two scans with the source orbited between scans the separation between data regions is about 2mm.

Figure 6:
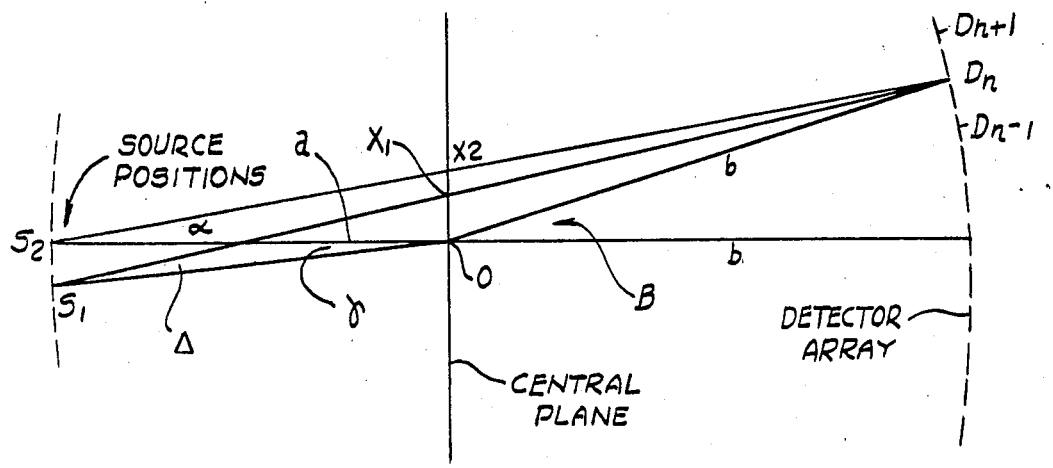
FIG. 6 is a schematic showing a relationship between a scanner x-ray tube and a portion of a scanner detector array to illustrate an interleaving of shadowgraph image data.

Turning now to FIG. 6, a geometric examination of shadowgraph data interleaving is presented. In FIG. 6, two source positions $S_1$ and $S_2$ are seen in relation to a detector array having representative detectors $D_n$, $D_{n+1}$, and $D_{n-1}$. The angle $\gamma$ represents the angle by which the scanning frame is rotated between longitudinal scans. Depicted in a central scanning plane are two points $X_1$, $X_2$. The following two equations represent the distance of these points $X_1$, $X_2$ from the origin 0 as a function of the FIG. 6 parameters.

$$X_2 = a \tan\left[\arcsin\left(\frac{b \sin \beta}{\sqrt{a^2 + b^2 + 2ab \cos\beta}}\right)\right]$$

$$X_1 = \frac{a \sin \Delta}{\cos (\gamma + \Delta)}, \text{ where}$$

$$\Delta = \arcsin\left[\frac{b \sin (\beta - \gamma)}{\sqrt{a^2 + b^2 + 2ab \cos (\beta - \gamma)}}\right]$$

These equations are derived from the law of sines and co-sines for the geometry of the FIG. 6 representation. A tabulation of these values for $X_1$, $X_2$ for representative detectors of a 600 detector scanner is summarized in Table I. That table shows the distance along the central plane from the origin to the locations $X_1$ and $X_2$ for various adjacent detectors for two source positions 0.3° degrees apart. By way of example, the designation $X_2$ (0,3) means the distance from $X_2$ to the origin in the central plane for the ray passing from the source at position $S_2$ to the third detector in the detector array.

TABLE I

| $X_2 = X_2(0,n)$ | | $X_1 = X_1(.3,n)$ | |
| --- | --- | --- | --- |
| $X_2(0,0) =$ | 1.91 mm | $X_1(.3,0) =$ | 0.0 mm |
| $X_2(0,1) =$ | 5.74 mm | $X_1(.3,1) =$ | 3.82 mm |
| $X_2(0,2) =$ | 9.56 mm | $X_1(.3,2) =$ | 7.65 mm |
| $X_2(0,3) =$ | 13.38 mm | | |
| $X_2(0,31) =$ | 122.02 mm | | |
| $X_2(0,32) =$ | 125.99 mm | $X_1(.3,32) =$ | 124.13 mm |
| $X_2(0,63) =$ | 256.45 mm | | |

TABLE I-continued

| $X_2 = X_2(0,n)$ | | $X_1 = X_1(.3,n)$ | |
| --- | --- | --- | --- |
| $X_2(0,64) =$ | 260.96 mm | $X_1(.3,64) =$ | 259.53 mm |

To obtain contrast data image information instead of enhanced resolution in a patient localization scan, the source position is left unchanged and two consecutive scans are conducted wherein the difference between shadowgraph data is caused by radio-opaque flow within the subject. In this application, contrast image information is obtained using digital subtraction techniques from digital radiography.

Several passes over a patient can be conducted to produce a sequence of images. If one image is used as a subtraction mask, a series of images showing contrast changes results. The ability to use a multiple pass patient imaging system may require registration of the images which are to be combined. Patient movement may require interactive real time registration to minimize motion artifacts in both contrast studies and interleaved scans. An article entitled "A Digital Video Image Processer for Real-Time X-ray Subtraction Imaging" to Kruger et al, Optical Engineering Vol. 17 No. 6, Nov.-Dec. 1978 discusses both digital subtraction and real time imaging and is incorporated herein by reference.

While the invention has been described with a degree of particularity, it is the intent that the invention include all modifications and/or alterations falling within the spirit or scope of the appended claims.

We claim:

1. In a computed tomography scanner having an x-radiation source that orbits about a rotation axis in an orbital path and irradiates a subject from different directions, said scanner including an array of x-radiation detectors on a side of said patient opposite said source; a method for generating a shadowgraph image of aid subject comprising the steps of:
   fixing the source at a first orbital position in relation to said subject;
   moving said subject in a longitudinal direction generally parallel to said rotation axis while irradiating said subject to obtain a first set of shadowgraph intensity data of a patient region of interest;
   indexing said source an angular amount along its orbital path from its first orbital position to a second orbital position and fixing said source in relation to said orbital path;
   moving said subject longitudinally along the longitudinal direction while again irradiating said subject to obtain a second set of shadowgraph intensity data from the patient region of interest; and
   interleaving the first and second sets of shadowgraph data and producing a combined shadowgraph image.

2. In a computed tomography scanner wherein an x-ray source orbits around a scanning axis passing longitudinally through a patient and directs radiation to and through the patient from a number of directions to a detector array, apparatus comprising:
   means for positioning said source at a first position relative to said patient;

means for relatively moving said source and detector array in unison longitudinally past a patient region of interest in a direction generally parallel to the scanning axis as the source irradiates said region;

means for converting intensity outputs from detectors in the array into a first shaowgraph data set;

means for orbiting said source to a second position and fixing said source relative to the patient prior to a reversal of relative longitudinal movement between the patient, the source and the array by said means for relatively moving while said means for converting produces a second shadowgraph data set; and means for interleaving the data from the first and second data sets to provide a shadowgraph data set having greater resolution than either said first or second data set.

3. The apparatus of claim 2 where the means for moving the source and array relative to the patient is a drive connected to a patient couch.

4. The apparatus of claim 2 where the detector array comprises at least an arc of of a circle and the means for orbiting said source rotates the x-ray source approximately one half the angular spacing between adjacent detector centers after said first shadowgraph set is detected.

5. A method for obtaining a localization image for a computed tomography scan comprising the steps of:
fixing an x-ray source in relation to a detecting array and a patient aperture;
positioning a patient at least partly within the aperture;
energizing the source to irradiate the patient with x-ray beams;
longitudinally moving the patient within the aperture relative the source and detector array;
sensing radiation intensity signals at detectors irradiated by radiation as the patient is moved;
storing the radiation signals to form a first shadowgraph data set;
orbitally indexing the source a small arc about the patient and again fixing said source in relation to the patient aperture;
again irradiating the patient as the patient is again longitudinally moved within the aperture relative to the source and detector array after source indexing to direct x-radiation through the patient along different beam paths;
again sensing radiation intensity signals as the patient moves to obtain a second shadowgraph data set, and
interleaving said first and second shadowgraph data sets to form a composite shadowgraph image having a resolution greater than the resolution of an image produced from either the first or second data sets alone.

6. The method of claim 5 where the patient is longitudinally moved in opposite directions as the first and second shadowgraph data sets are sensed.

7. The method of claim 5 where the second shadowgraph data set is stored prior to the interleaving of said first and second data sets.

8. The method of claim 5 where the composite image image is displayed to help locate structure within the patient prior to a computed tomography scan.

9. Apparatus for generating a patient localization image to aid in positioning a patient in a patient examination position for a computed tomography scan comprising:
means, for positioning an x-ray source relative the patient examination position;
means for energizing the source to irradiate said patient position;
a patient support for supporting a patient in the patient examination position;
means for moving the patient support longitudinally through the patient examination position;
means for sensing radiation intensity signals passing through the patient examination position as the patient support is moved;
means for storing the radiation signals to form a shadowgraph data set;
means for orbitally indexing the source a small arc about the patient position to alter the paths taken by radiation originating at the source and passing through the patient examination position; and
means for interleaving a stored shadowgraph data set with a second shadowgraph data set obtained after the source has been moved through the small arc as said means for moving longitudinally moves the patient support through the patient examination position, said means for combining forming a composite image from the stored and the second shadowgraph data sets.

10. A diagnostic x-ray medical examination process performed with a computed tomography scanner comprising:
(a) placing an x-ray tube forming a part of the scanner in a first predetermined fixed position;
(b) moving a patient couch longitudinally along a path which is generally axial of a scanner defined patient aperture;
(c) energiizng the tube as the couch is moved and concurrently repetitively collecting data in coordination with the couch movement to produce a first collected data set from which at least a partial shadow image can be produced;
(d) storing the first data set;
(e) orbiting the tube from its first to a second predetermined fixed position;
(f) again moving the couch longitudinally along its path while the tube is concurrently energized;
(g) collecting further data in coordination with the movement of step (f) and as step (f) is performed to produce a second data set from which at least a portion of a shadow image can be produced;
(h) interleaving the data sets; and
(i) producing a shadow image from the interleaved data sets.

* * * * *